US012765833B2

(12) United States Patent
Kwak et al.

(10) Patent No.: US 12,765,833 B2
(45) Date of Patent: Oct. 20, 2026

(54) METHOD AND APPARATUS FOR ANALYZING SPECTRUM OF AUDITORY THERAPY FREQUENCIES

(71) Applicant: Sound Vaccine, Inc., Daejeon (KR)

(72) Inventors: Eun Yee Kwak, Seoul (KR); Woo Jin Doo, Goyang-si (KR); Song Hwa Kim, Seoul (KR); Sangyeop Kwak, Seoul (KR)

(73) Assignee: Sound Vaccine, Inc., Daejeon (KR)

( * ) Notice: Subject to any disclaimer, the term of this patent is extended or adjusted under 35 U.S.C. 154(b) by 1100 days.

(21) Appl. No.: 17/641,986

(22) PCT Filed: Oct. 8, 2020

(86) PCT No.: PCT/KR2020/013769
§ 371 (c)(1),
(2) Date: Mar. 10, 2022

(87) PCT Pub. No.: WO2021/075795
PCT Pub. Date: Apr. 22, 2021

(65) Prior Publication Data

US 2022/0370007 A1 Nov. 24, 2022

(30) Foreign Application Priority Data

Oct. 16, 2019 (KR) ........................ 10-2019-0128144

(51) Int. Cl.
*A61B 5/00* (2006.01)
*A61B 5/12* (2006.01)

(52) U.S. Cl.
CPC .............. *A61B 5/4836* (2013.01); *A61B 5/12* (2013.01); *A61B 5/7228* (2013.01); *A61B 5/7235* (2013.01)

(58) Field of Classification Search
CPC ....... A61B 5/4836; A61B 5/12; A61B 5/7228; A61B 5/7235; A61B 5/121; A61B 5/123;
(Continued)

(56) References Cited

U.S. PATENT DOCUMENTS

| | | | | |
|---|---|---|---|---|
| 2004/0131200 A1* | 7/2004 | Davis | .................. | H04R 25/505 381/317 |
| 2008/0221719 A1* | 9/2008 | Margolis | ............. | A61B 5/7264 73/585 |

(Continued)

FOREIGN PATENT DOCUMENTS

| | | |
|---|---|---|
| KR | 10-2006-0083318 A | 7/2006 |
| KR | 10-2009-0060598 A | 6/2009 |

(Continued)

OTHER PUBLICATIONS

International Search Report_PCT/KR2020/013769.
(Continued)

*Primary Examiner* — Jennifer Robertson
*Assistant Examiner* — Elina Sohyun Jang

(57) ABSTRACT

An apparatus for auditory therapy frequency spectrum analysis includes: a processor and a memory connected to the processor, wherein the memory stores program instructions executable by the processor to receive a hearing threshold of a user for each of n frequency bands in which an audible frequency band is divided with 1/k octave resolution, calculate n hearing threshold representative values for each of the n frequency bands according to a preset criterion, determine a group to which the user belongs by using the calculated n hearing threshold representative values, and determine acoustic stimulus signals of frequency bands sequentially required for the user to be treated based on the determined group.

11 Claims, 4 Drawing Sheets

(58) Field of Classification Search
CPC ......... A61F 11/00; H04R 25/50; H04R 25/70; A61N 1/36038
See application file for complete search history.

(56) References Cited

U.S. PATENT DOCUMENTS

| | | | | |
|---|---|---|---|---|
| 2009/0149916 A1* | 6/2009 | Kwak | A61F 11/00 | 607/55 |
| 2010/0076338 A1* | 3/2010 | Kwak | A61B 5/125 | 600/559 |

FOREIGN PATENT DOCUMENTS

| | | |
|---|---|---|
| KR | 10-2013-0022944 A | 3/2013 |
| KR | 10-2013-0079945 A | 7/2013 |
| KR | 10-2013-0083730 A | 7/2013 |

OTHER PUBLICATIONS

Office Action from Korean Intellectual Property Office for Application No. 10-2019-0128144 Dated Nov. 13, 2019.
Written Opinion of International Search Authority_PCT/KR2020/013769.

* cited by examiner

【FIGURE 1】
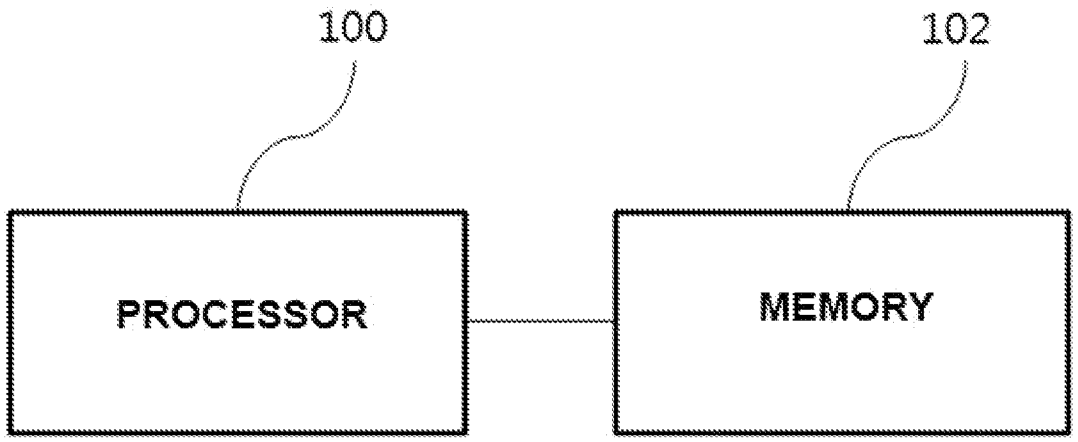
【FIGURE 2】
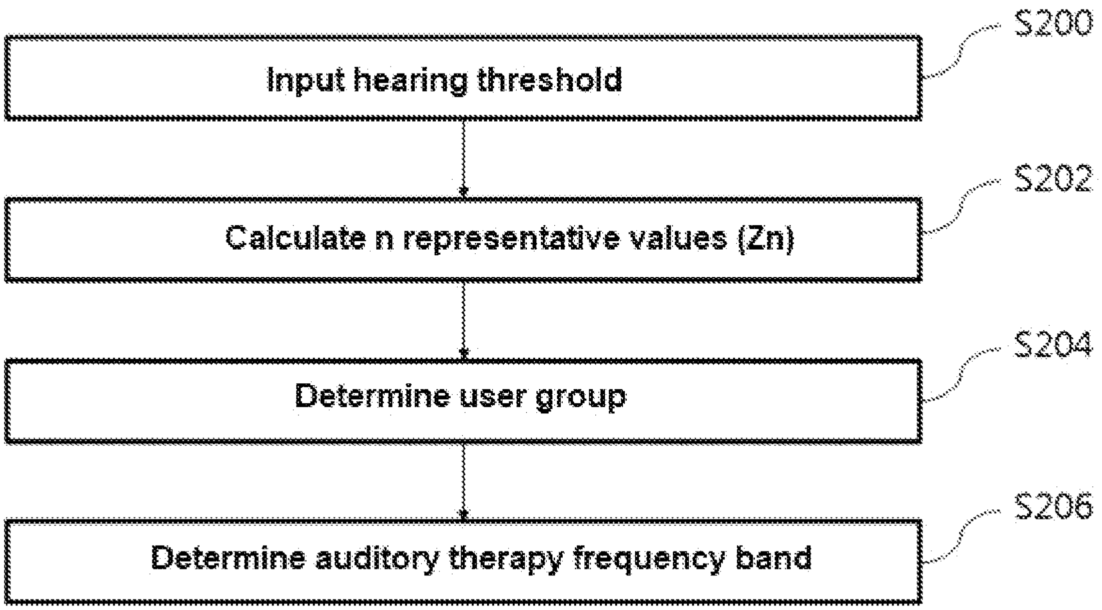

【FIGURE 3】
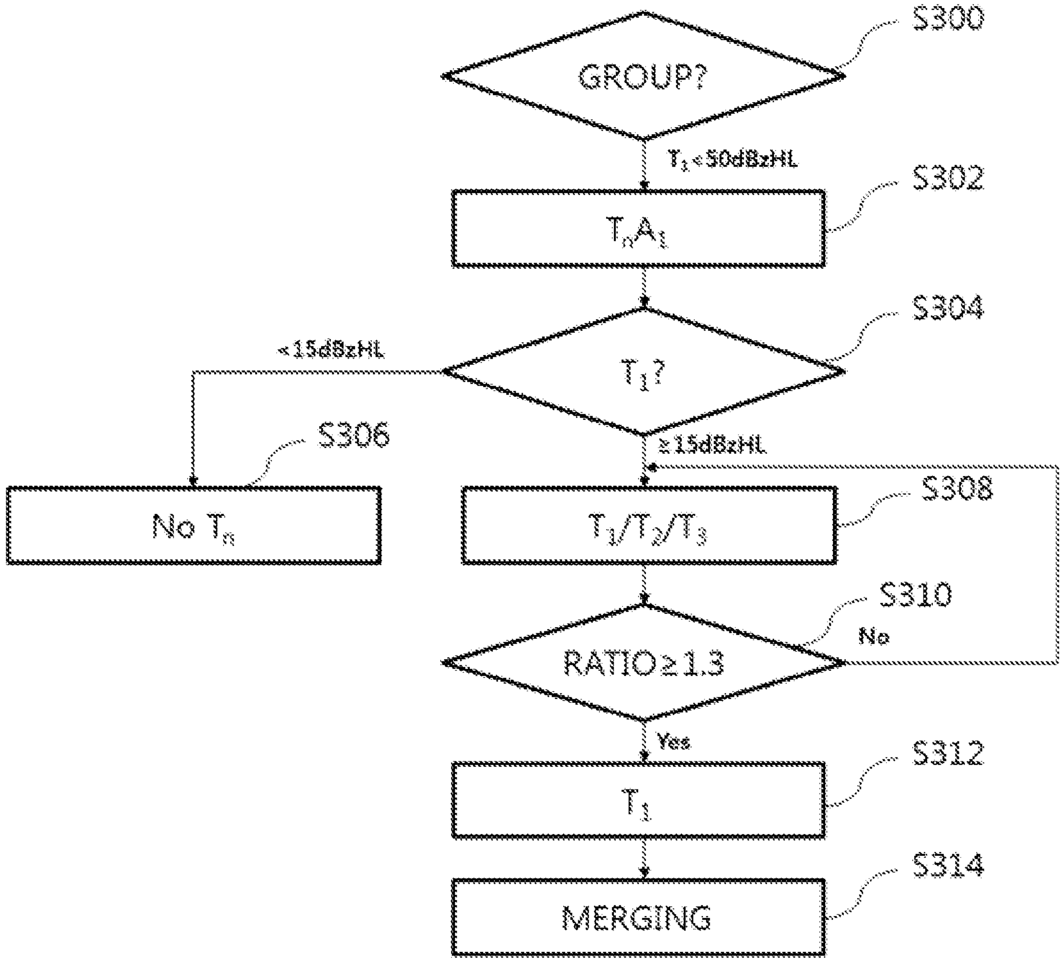

【FIGURE 4】
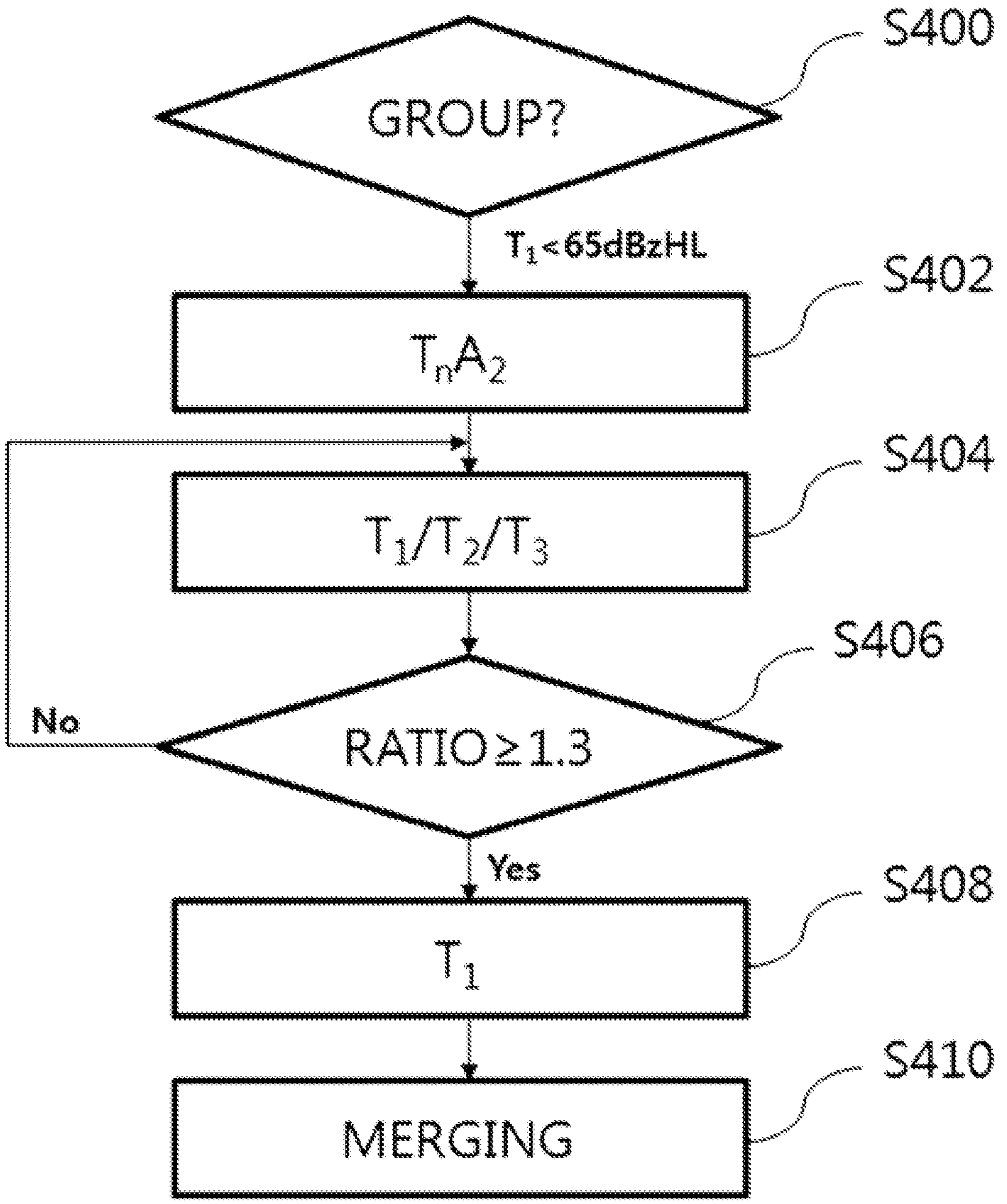

【FIGURE 5】
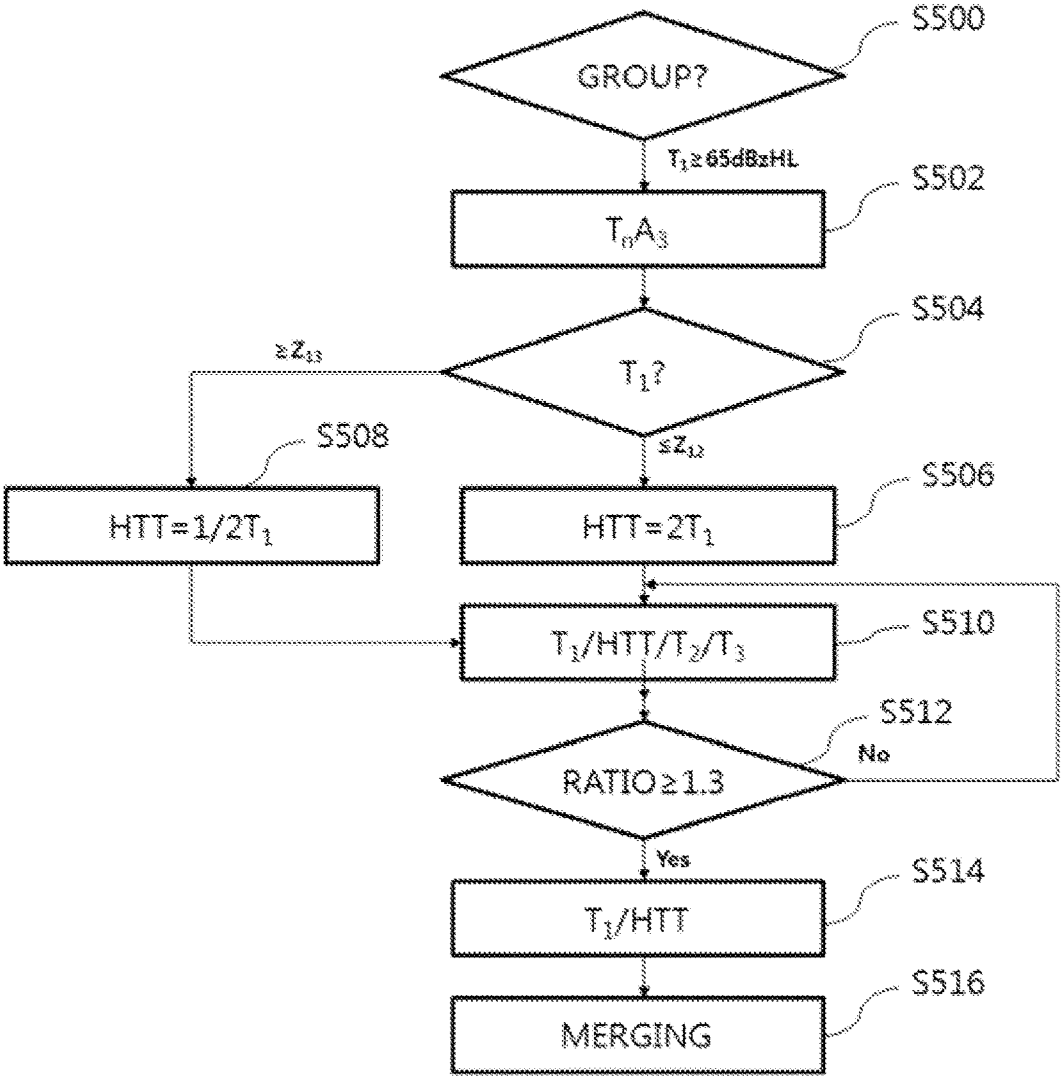

METHOD AND APPARATUS FOR ANALYZING SPECTRUM OF AUDITORY THERAPY FREQUENCIES

CROSS-REFERENCE TO RELATED APPLICATIONS

This application is a National Stage Entry of PCT International Application No. PCT/KR2020/013769, which was filed on Oct. 8, 2020, and which claims priority from and the benefit of Korean Patent Application 10-2019-0128144, filed with the Korean Intellectual Property Office on Oct. 16, 2019, the disclosure of which are hereby incorporated by reference in its entirety.

TECHNICAL FIELD

The present invention relates to auditory therapy frequency spectrum analysis method and apparatus.

BACKGROUND ART

All organs that transmit sound to the brain are collectively called the auditory organ.

The auditory organ is largely divided into the outer ear, the middle ear, and the inner ear, and the sound introduced from the outside through the outer ear vibrates in the eardrum and is transmitted to the cochlea of the inner ear through the middle ear.

Auditory hair cells (hereinafter referred to as "auditory cells") are arranged in the basilar membrane of the cochlea, and the total number of auditory cells arranged uniformly on the basilar membrane is approximately 15,000. The length of the basilar membrane is approximately 2.5 to 3 cm, and the auditory cells located at the starting part of the basilar membrane sense high frequencies, and the auditory cells located at the end of the basilar membrane sense low frequencies.

This is called frequency specificity of the auditory cells, and the frequency specificity resolution at the most ideal stimulation intensity level is known to reach a range of approximately 0.2 mm (0.5 semitone) on the basilar membrane.

Meanwhile, in recent years, many people have sensorineural hearing loss diseases due to the increased use of portable audio devices and exposure to various noises. The sensorineural hearing loss is the hearing degradation caused by damage to auditory cells or auditory nerves, and is caused by aging, noise exposure, drug side effects, genetic factors, and the like.

The sensorineural hearing loss is classified into mild, moderate, severe, and profound hearing loss according to the degree of hearing impairment, and in general, ordinary conversation is difficult with moderate hearing loss or higher.

Currently, it has been estimated that about 10% of the world's population has mild hearing loss symptoms enough to feel their own hearing degeneration, and it has been estimated that the scale of patients with severe hearing loss of moderate or higher is approximately 260 million or more only in developing countries.

In the related art, methods for treating hearing loss diseases have not been introduced, and only a hearing aid is provided as a hearing aid device related to hearing loss.

The hearing aid is a device that simply amplifies external sounds to hear the sounds loudly, but there is a problem that the hearing aid does not fundamentally prevent the hearing degeneration, and rather further degenerates the hearing of a hearing aid user due to the amplified sounds.

Therefore, there is an urgent need for methods capable of fundamentally treating hearing loss diseases rather than using the hearing aid.

In addition, in addition to the hearing loss, recently, interest in the treatment of tinnitus, which feels sound even without external stimuli, has increased.

The present applicants have already confirmed that for treatment of hearing loss and tinnitus, acoustic stimulus signals (modulated acoustic signals) are provided in a frequency band corresponding to damaged auditory cells to treat the hearing loss and tinnitus.

However, the existing methods have a problem that it takes a long time in processes of tracking a frequency band in which hearing loss and tinnitus occur with high resolution and determining acoustic stimulus signals in the corresponding frequency band.

DISCLOSURE

Technical Problem

In order to solve the problems in the related art, the present invention has been made in an effort to provide auditory therapy frequency spectrum analysis method and apparatus capable of rapidly determining and generating high-resolution modulated acoustic signals.

Technical Solution

To achieve the above objects, an aspect of the present invention is directed to provide an auditory therapy frequency spectrum analysis apparatus including: a processor; and a memory connected to the processor, wherein the memory stores program instructions executable by the processor to receive a hearing threshold of a user for each of n frequency bands in which an audible frequency band is divided with 1/k octave resolution, calculate n hearing threshold representative values for each of the n frequency bands according to a preset criterion, determine a group to which the user belongs by using the calculated n hearing threshold representative values, and determine acoustic stimulus signals of frequency bands sequentially required for the user to be treated based on the determined group.

Each hearing threshold representative value may be calculated as an average value of a hearing threshold of a first frequency band among the plurality of n divided frequency bands and the hearing thresholds of the plurality of frequency bands adjacent to the first frequency band, and the acoustic stimulus signal may be a modulated acoustic signal having the first frequency band and the plurality of adjacent frequency band ranges.

The hearing threshold representative value for the first frequency band may be calculated as an average value of the hearing threshold of the first frequency band and the hearing thresholds of two to four adjacent frequency bands adjacent to the first frequency band.

The group to which the user belongs may be determined according to a first threshold corresponding to a lower limit of the n hearing threshold representative values and a second threshold corresponding to an upper limit thereof.

The program instructions may sort the n hearing threshold representative values in descending order, generate a plurality of hearing threshold representative value lists in upper order among the hearing threshold representative values sorted in descending order, and determine an acoustic stimulus signal of a frequency band sequentially required to be treated using a difference in frequency ratio of the frequency band range corresponding to each of the plurality of hearing threshold representative values included in the list.

The program instructions may delete a second hearing threshold representative value from the list when a difference in frequency ratios between a first hearing threshold representative value corresponding to an upper order among the plurality of hearing threshold representative values and the second hearing threshold representative value corresponding to a lower order thereof is smaller than a preset value.

The program instructions may determine the group of the user as a first group when all of the n hearing threshold representative values are smaller than the first threshold, determine whether there is at least one hearing threshold representative value corresponding between a third threshold and a fourth threshold among the n hearing threshold representative values, generate a plurality of hearing threshold representative value lists in upper order among the hearing threshold representative values corresponding between the third threshold and the fourth threshold, and determine an acoustic stimulus signal of a frequency band sequentially required to be treated using a difference in frequency ratio of the frequency band range corresponding to each of the plurality of hearing threshold representative values included in the list.

The program instructions may determine the group of the user as a second group when at least one of the n hearing threshold representative values is greater than the first threshold and all of the n hearing threshold representative values are smaller than the second threshold.

The program instructions may determine the group of the user as a third group when at least one of the n hearing threshold representative values is greater than the second threshold.

The program instructions may determine whether a frequency band of the highest hearing threshold representative value having the largest value among the hearing threshold representative values sorted in descending order among the n hearing threshold representative values belongs to a preset frequency band range, determine a frequency corresponding to twice the frequency band of the highest hearing threshold representative value as a harmonic template target (HTT) of the highest hearing threshold representative value when the frequency band of the highest hearing threshold representative value belongs to the preset frequency band range, and determine a frequency corresponding to ½ times the frequency band of the highest hearing threshold representative value as a harmonic template target (HTT) of the highest hearing threshold representative value when the frequency band of the highest hearing threshold representative value does not belong to the preset frequency band range.

The program instructions may delete the second hearing threshold representative value from the list when a frequency ratio of the first hearing threshold representative value or the harmonic template target corresponding to the upper order among the plurality of hearing threshold representative values and the second hearing threshold representative value corresponding to the lower order thereof is smaller than the preset value.

According to another aspect of the present invention, there is provided an auditory therapy frequency spectrum analysis method as a method for analyzing an auditory therapy frequency spectrum in an apparatus comprising a processor and a memory connected to the processor, the method comprising steps of: receiving a hearing threshold of a user for each of n frequency bands in which an audible frequency band is divided with 1/k octave resolution; calculating n hearing threshold representative values for each of the n frequency bands according to a preset criterion; determining a group to which the user belongs by using the calculated n hearing threshold representative values; and determining acoustic stimulus signals of frequency bands sequentially required for the user to be treated based on the determined group.

According to yet another aspect of the present invention, there is provided a program stored in a recording medium for performing the method.

Advantageous Effects

According to the present invention, since the average value of the hearing thresholds of individual frequency bands to be tested for hearing is calculated as a representative value to determine a group to which the user belongs and determine frequency bands sequentially required to be treated according to a hearing threshold representative value in the determined group, it is possible to rapidly determine an auditory therapy frequency spectrum.

DESCRIPTION OF DRAWINGS

FIG. 1 is a diagram illustrating a configuration of an auditory therapy frequency spectrum analysis apparatus according to an exemplary embodiment of the present invention.

FIG. 2 is a flowchart schematically illustrating an auditory therapy frequency spectrum analysis process according to an exemplary embodiment of the present invention.

FIG. 3 is a flowchart illustrating a process of classifying a group and determining a frequency band required for auditory therapy according to a preferred exemplary embodiment of the present invention.

FIG. 4 is a diagram illustrating a process of determining an auditory therapy frequency spectrum of a user corresponding to a group $A_2$ according to an exemplary embodiment of the present invention.

FIG. 5 is a diagram illustrating a process of determining an auditory therapy frequency spectrum of a user corresponding to a group $A_3$ according to an exemplary embodiment of the present invention.

BEST MODE

The present invention may have various modifications and various exemplary embodiments and specific exemplary embodiments will be illustrated in the drawings and will be described in detail. However, the present invention is not limited to specific exemplary embodiments, and it should be understood that the present invention covers all the modifications, equivalents and replacements included within the idea and technical scope of the present invention. In describing each drawing, like reference numerals were used for like components.

It should be understood that, when it is described that a component is "coupled" or "connected" to the other component, the component may be directly coupled or connected to the other component, but there may be another component therebetween. In contrast, it should be understood that, when it is described that a component is "directly coupled" or "directly connected" to the other component, it should be understood that no component is present therebetween.

Terms used herein are used only to describe specific exemplary embodiments, and are not intended to limit the present invention. Singular expressions used herein include plurals expressions unless they have definitely opposite meanings in the context. The terms such as "comprising, or "having" are inclusive and therefore specify the presence of stated features, integers, steps, operations, elements, and/or components, but do not preclude the presence or addition of one or more other features, integers, steps, operations, elements, components, and/or groups thereof.

Unless otherwise contrarily defined, all terms used herein including technological or scientific terms have the same meanings as those generally understood by a person with ordinary skill in the art. Terms which are defined in a generally used dictionary should be interpreted to have the same meaning as the meaning in the context of the related art, and are not interpreted as ideal or excessively formal meanings unless otherwise defined in the present application.

Hereinafter, a preferable exemplary embodiment of the present invention will be described in detail with reference to the accompanying drawings. In describing the present invention, like reference numerals will be used for like means regardless of the drawing number in order to facilitate an overall understanding.

FIG. 1 is a diagram illustrating a configuration of an auditory therapy frequency spectrum analysis apparatus according to an exemplary embodiment of the present invention.

As illustrated in FIG. 1, the auditory therapy frequency spectrum analysis apparatus (hereinafter, referred to as an 'analysis apparatus') according to the exemplary embodiment may include a processor 100 and a memory 102.

The processor 100 may include a central processing unit (CPU) capable of executing a computer program, other virtual machines, or the like.

The memory 102 may include a nonvolatile storage device such as a fixed hard drive or a detachable storage device. The detachable storage device may include a compact flash unit, a USB memory stick, etc. The memory 102 may also include volatile memories such as various types of random access memories.

According to an exemplary embodiment of the present invention, the processor 100 uses program instructions stored in the memory 102 to rapidly determine a frequency band in which hearing loss or tinnitus treatment is required.

The analysis apparatus according to the exemplary embodiment receives a hearing threshold of a user for each of n frequency bands in which an audible frequency band is divided with 1/k octave resolution, calculates n hearing threshold representative values for each of the n frequency bands according to a preset criterion, determines a group to which the user belongs by using the calculated n hearing threshold representative values, and determines acoustic stimulus signals of frequency bands sequentially required for the user to be treated based on the determined group.

The audible frequency band may be in the range of 1,000 to 12,000 Hz, and the audible frequency Preferably, the audible frequency band may be divided with 1/12 octave resolution, and the frequency band to be tested for hearing may be divided into 43 frequency bands.

The n frequency bands may be defined as indexes of frequency bands to be tested for hearing.

In the exemplary embodiment, the hearing threshold representative value may be an average value of a hearing threshold of a first frequency band among the plurality of frequency bands and the hearing thresholds of the plurality of frequency bands adjacent thereto, and as described above, when the audible frequency band is divided into n frequency bands, n representative values are calculated.

The acoustic stimulus signal according to the exemplary embodiment is a modulated acoustic signal having the first frequency band and the plurality of adjacent frequency band ranges.

According to the exemplary embodiment, a representative value concept $Z_n$ (unit dBzHL) corresponding to the average value of the hearing thresholds of the plurality of frequency bands rather than the hearing threshold of each frequency band to be treated for hearing is introduced to rapidly determine a frequency band for auditory therapy.

In addition, the group to which the user belongs may include a plurality of groups according to a first threshold corresponding to a lower limit of the representative values and a second threshold corresponding to an upper limit thereof.

Preferably, the group may include three groups, $A_1$ to $A_3$ groups.

Here, the first threshold may be 50.00 dBzHL, and the second threshold may be 65.00 dBzHL.

Hereinafter, an auditory therapy frequency spectrum analysis process will be described in detail with reference to the drawings.

FIG. 2 is a flowchart schematically illustrating an auditory therapy frequency spectrum analysis process according to an exemplary embodiment of the present invention.

First, the hearing threshold of the user is input (Step 200).

1,000 to 12,000 Hz are divided into frequency bands with 1/12 octave resolution, and a modulated acoustic signal corresponding to each frequency band is presented at random left and right to measure a hearing threshold for each divided frequency band.

Here, the modulated acoustic signal is an acoustic stimulus signal provided for the hearing therapy of the user later, and may consist of at least one of amplitude-modulated sound, frequency-modulated sound, pulsed sound, continuous sound, and amplitude-modulated narrow-band noise, or a combination thereof.

In addition, in order to increase the efficiency of hearing threshold measurement, first, a pre-screening test is performed at 20 dB size intervals with 1/3 octave resolution, and the hearing threshold is measured again with high resolution of 1/12 octave with respect to the hearing threshold determined in the pre-screening test.

When 1,000 to 12,000 Hz is divided with 1/12 octave resolution, the audible frequency band may be divided into 43 frequency bands, and the hearing threshold of the user is defined as a size $Y_n$ of the hearing threshold for each of the 43 frequency bands $X_n$. That is, the hearing threshold is expressed as a pair $(X_n, Y_n)$ of the frequency band and the hearing threshold size, wherein n is 1 to 43.

The analysis apparatus according to the exemplary embodiment calculates n representative values $Z_n$ by using the hearing threshold of the user (Step 202).

Step 202 is a process of calculating an average value of hearing thresholds of one frequency band and one or more frequency bands adjacent thereto for each of the audible frequency bands $X_1$ to $X_{43}$.

Step 202 is performed individually for all n frequency bands.

For example, a representative value may be calculated using hearing thresholds of two frequency bands adjacent to each other on the left and right sides with respect to one frequency band. In this case, the average value of the hearing thresholds of the frequency bands corresponding to $X_{k-2}$ and $X_{k-1}$ on the left side and $X_{k+1}$ and $X_{k+2}$ on the right side based on $X_k$ is calculated as a representative value.

At this time, since the first frequency band and the 43-th frequency band have two adjacent frequency bands on the left and right, the average value of the hearing thresholds of the three frequency bands becomes a representative value, and since the second frequency band and the 42-th frequency band have three adjacent frequency bands, the average value of the hearing thresholds of the four frequency bands becomes a representative value.

In the exemplary embodiment, representative values of hearing thresholds of the plurality of frequency bands adjacent to each other are used, which are defined as the concept of Z hearing, and the unit of the Z hearing value is defined as dBzHL.

As such, when the representative value is introduced, the time for determining the frequency band for hearing therapy may be further shortened.

Thereafter, the analysis device determines a group to which the corresponding user belongs by using the n representative values and one or more thresholds (Step 204).

For example, the plurality of groups may be classified according to the degree of hearing loss, and the thresholds for classifying the group may include a first threshold corresponding to a lower limit of the representative values and a second threshold corresponding to an upper limit thereof.

For example, the first threshold may be 50.00 dBzHL, and the second threshold may be 65.00 dBzHL, but are not necessarily limited thereto.

The analysis apparatus determines the frequency bands sequentially required for auditory therapy based on a different criterion according to the group classified in Step 204 (Step 206).

Steps 204 to 206 will be described below again.

FIG. 3 is a flowchart illustrating a process of classifying a group and determining a frequency band required for auditory therapy according to a preferred exemplary embodiment of the present invention.

In FIG. 3, the process of classifying the group into three groups such as $A_1$ to $A_3$ according to the first and second thresholds and determining the auditory therapy frequency band of the user belonging to the group $A_1$ will be mainly described.

Referring to FIG. 3, as illustrated in FIG. 2, whether the group to which the user belongs corresponds to any one of the groups $A_1$ to $A_3$ is determined by comparing the representative value $Z_n$ with the first and second thresholds (Step 300).

As described above, the first threshold may be 50.00 dBzHL, and the second threshold may be 65.00 dBzHL.

In Step 300, when there is no representative value of 50.00 dBzHL or more among the n representative values (hereinafter referred to as Z values), the group is determined as the group $A_1$, and when there are one or more values of 50.00 dBzHL or more among the n Z values and there is no value of 65.00 dBzHL or more, the group is determined as the group $A_2$.

In addition, if there are one or more values of 65.00 dBzHL or more among the n Z values, the group is determined as the group $A_3$.

When it is determined that the user belongs to the group $A_1$, all of the n Z values are sorted in descending order (Step 302).

In the exemplary embodiment, a list in which the representative values of the group $A_1$ are sorted in descending order is defined as $T_nA_1$, and when there are a plurality of identical representative values in $T_nA_1$, the representative values are sorted in descending order according to the size of the frequency band of each representative value.

According to the exemplary embodiment, it is determined whether there is a Z value corresponding to 15.00 dBzHL or more and 49.99 dBzHL or less in $T_nA_1$ (Step 304).

Step 304 is a process of determining a user who does not require auditory therapy due to a low hearing threshold using the third and fourth thresholds, and when there is no Z value corresponding to 15.00 dBzHL or more and 49.99 dBzHL or less, $T_nA_1$ is deleted (Step 306).

On the other hand, when there are one or more Z values corresponding to 15.00 dBzHL or more and 49.99 dBzHL or less corresponding to the third and fourth thresholds, a plurality of $T_n$ values are determined in upper order (Step 308).

In FIG. 3, the determining of three $T_n$ values corresponding to upper order is exemplarily described, and in Step 308, $T_1$ to $T_3$ corresponding to upper order are determined.

Next, it is determined whether a difference in frequency ratios of the frequency band ranges corresponding to $T_1$ to $T_3$ is greater than a preset value (Step 310).

Here, the difference in frequency ratios may be defined as a ratio difference between the center frequencies of different representative values.

As described above, the representative value may have one frequency band (the first frequency band) and a plurality of frequency band ranges adjacent thereto, wherein the center frequency may be defined as the center frequency of the first frequency band.

In Step 310, the preset value may be 1.3, and if the differences $T_1/T_2$, $T_2/T_3$, $T_1/T_3$ in frequency ratios of each of $T_1$, $T_2$, and $T_3$ are smaller than 1.3, the lower $T_n$ value is deleted from $T_nA_1$ (Step 312).

For example, if the difference in frequency ratios between $T_1$ and $T_2$ is smaller than 1.3, $T_2$ is deleted from $T_nA_1$, if the difference in frequency ratios between $T_2$ and $T_3$ is smaller than 1.3, $T_3$ is deleted from $T_nA_1$, and even in the case of $T_1$ and $T_3$, $T_3$ is deleted from $T_nA_1$.

When at least one $T_n$ is deleted in Step 312, the value corresponding to the next rank becomes $T_n$, and Steps 310 to 312 are repeatedly performed.

That is, Steps 310 to 312 are repeatedly performed until the differences in frequency ratios of $T_1$, $T_2$, and $T_3$ of $T_nA_1$ are greater than 1.3.

Thereafter, a signal corresponding to $T_1$ is merged with the acoustic stimulus signal of the user, that is, the modulated acoustic signal to be provided to the user (Step 314).

According to the exemplary embodiment, the acoustic stimulus signal is preferentially provided for the frequency band with the largest Z value for the user belonging to the group $A_1$, and after a preset period, while the processes of FIGS. 2 and 3 are repeatedly performed again, it is determined whether an acoustic stimulus signal having a different frequency band range is provided and an acoustic stimulus signal having the same frequency band range as the previous process is provided.

According to the exemplary embodiment, since the representative value of binding frequencies to be tested is used instead of the individual frequencies to be tested for hearing, the acoustic stimulus signal is not one of the 43 divided frequencies, but is a signal corresponding to approximately 5 frequency bands to be tested for hearing.

FIG. 4 is a diagram illustrating a process of determining an auditory therapy frequency spectrum of a user corresponding to a group $A_2$ according to an exemplary embodiment of the present invention.

Referring to FIG. 4, when there are one or more values of 50.00 dBzHL or more among the n Z values and there is no value of 65.00 dBzHL or more, the group is determined as a group $A_2$ (Step 400), and representative values of 65.00 dBzHL or less are sorted in descending order (Step 402).

In the exemplary embodiment, a list in which the representative values of the group $A_2$ are sorted in descending order is defined as $T_nA_2$, and when there are a plurality of identical representative values in $T_nA_2$, the representative values are sorted in descending order according to the size of the frequency band of each representative value.

From the Z values sorted in descending order, $T_1$ to $T_3$ corresponding to the upper order are determined (Step 404).

Next, it is determined whether a difference in frequency (center frequency) ratios of corresponding to $T_1$ to $T_3$ is greater than a preset value (Step 406).

In Step 404, the preset value may be 1.3, and if the differences $T_1/T_2$, $T_2/T_3$, $T_1/T_3$ in frequency ratios of each of $T_1$, $T_2$, and $T_3$ are smaller than 1.3, the lower $T_n$ value is deleted from $T_nA_2$.

For example, if the difference in frequency ratios between $T_1$ and $T_2$ is smaller than 1.3, $T_2$ is deleted from $T_nA_2$, if the difference in frequency ratios between $T_2$ and $T_3$ is smaller than 1.3, $T_3$ is deleted from $T_nA_2$, and even in the case of $T_1$ and $T_3$, $T_3$ is deleted from $T_nA_2$.

When at least one $T_n$ is deleted in Step 406, the value corresponding to the next rank becomes $T_n$, and Steps 404 to 406 are repeatedly performed to determine a frequency band of $T_1$ requiring auditory therapy preferentially (Step 408).

Thereafter, a signal corresponding to $T_1$ is merged with the acoustic stimulus signal of the user, that is, the modulated acoustic signal to be provided to the user (Step 410).

FIG. 5 is a diagram illustrating a process of determining an auditory therapy frequency spectrum of a user corresponding to a group $A_3$ according to an exemplary embodiment of the present invention.

Referring to FIG. 5, when the number of 65.00 dBzHL or more is one or more among the n Z values, the group is determined as a group $A_3$ (Step 500), and all representative values are sorted in descending order.

In the exemplary embodiment, a list in which the representative values of the group $A_3$ are sorted in descending order is defined as $T_nA_3$, and when there are a plurality of identical representative values in $T_nA_3$, the representative values are sorted in descending order according to the size of the frequency band of each representative value (Step 502).

From the Z values sorted in descending order, it is determined whether a frequency band of $T_1$ corresponding to the highest order belongs to a preset frequency band range (Step 504).

Here, the preset frequency band range may be an index n=1 to 12.

In Step 506, if the frequency band of $T_1$ is less than or equal to a frequency band corresponding to n=12, a frequency corresponding to twice the frequency band of $T_1$ is determined as a harmonic template target (HTT) of $T_1$, which is defined as $2T_1$ (Step 506).

On the other hand, in Step 504, if the frequency band of $T_1$ corresponds to a frequency band corresponding to n=13 or more, a frequency corresponding to ½ times of the frequency band of $T_1$ is determined as a harmonic template target (HTT) of $T_1$, which is defined as $½T_1$ (Step 508).

When the audible frequency band 1,000 to 12,000 Hz is divided with 1/12 octave resolution, a center frequency corresponding to n=12 is 1976 Hz, and a center frequency corresponding to n=13 is 2093 Hz.

Next, in $T_nA_3$, $T_1$ to $T_3$ corresponding to the upper order are determined (Step 510).

It is determined whether a difference in frequency ratios of the frequency band ranges corresponding to $T_1$ to $T_3$ determined in Step 510 and HTT is greater than a preset value (Step 512).

In Step 512, the preset value may be 1.3, and if the differences $T_1/T_2$, $T_2/T_3$, $T_1/T_3$, HTT/$T_2$, and HTT/$T_3$ in frequency ratios of each of $T_1$, $T_2$, $T_3$, and HTT are smaller than 1.3, the lower $T_n$ value is deleted from $T_nA_3$ (Step 514).

When at least one $T_n$ is deleted in Step 512, the value corresponding to the next rank becomes $T_n$, and Steps 514 to 516 are repeatedly performed.

Next, $T_1$ and HTT are merged to be provided to the user (Step 516).

When the modulated acoustic signal corresponding to the auditory therapy frequency band is provided, if the Z value of $T_1$ is 40 dBzHL or more, the corresponding volume is merged as it is, but if the Z value of $T_1$ is 40 dBzHL or less, the merging sound source is amplified by a predetermined dB (e.g., 25 dB) or more to be provided to the user.

The exemplary embodiments of the present invention described above are disclosed for purposes of illustration, and it will be apparent to those skilled in the art that various modifications, additions, and substitutions are possible within the spirit and scope of the present invention and these modifications, changes, and additions should be considered as falling within the scope of the following claims.

The invention claimed is:

1. An auditory therapy frequency spectrum analysis apparatus comprising:
- a processor; and
- a memory connected to the processor,
- wherein the memory stores program instructions executable by the processor to
- divide an audible frequency band into an n number of frequency bands with a 1/k octave resolution,
- receive a hearing threshold of a user for each of the n number of frequency bands,
- calculate a hearing threshold representative value for each of the n number of frequency bands, wherein the hearing threshold representative value for each of the n number of frequency bands is calculated as an average value of a hearing threshold of a first frequency band among the n number of frequency bands and hearing thresholds of a plurality of frequency band adjacent to the first frequency band,
- determine a group, among a plurality of groups, to which the user belongs by using the calculated hearing threshold representative value for each of the n number of frequency bands, and
- determine an acoustic stimulus signal for the user according to the determined group, generate the acoustic stimulus signal for providing to the user to treat hearing loss or tinnitus,
- wherein the acoustic stimulus signal is a modulated acoustic signal having the first frequency band and the plurality of frequency bands adjacent to the first frequency band,
- wherein the user is assigned to one of the plurality of groups according to a first threshold corresponding to a lower limit of the hearing threshold representative value for each of the n number of frequency bands and a second threshold corresponding to an upper limit of the hearing threshold representative value for each of the n number of frequency bands, wherein each of the plurality of groups includes a plurality of frequency bands and a plurality of hearing threshold representative values corresponding to the plurality of frequency bands within the group, wherein the plurality of hearing threshold representative values within each of the plurality of groups are sorted in descending order, and wherein the acoustic stimulus signal is determined by comparing a difference in ratio between the plurality of hearing threshold representative values within the assigned group and a preset value of 1.3.

2. The auditory therapy frequency spectrum analysis apparatus of claim 1, wherein the hearing threshold representative value for the first frequency band is an average value of a hearing threshold of the first frequency band and hearing thresholds of two to four frequency bands adjacent to the first frequency band.

3. The auditory therapy frequency spectrum analysis apparatus of claim 1, wherein the auditory therapy frequency spectrum analysis apparatus is configured to sort a first hearing threshold representative value within the assigned group in descending order above a second hearing threshold representative value within the assigned group, to compare a ratio between the first hearing threshold representative value and the second hearing threshold representative value to the preset value of 1.3, and to delete the second hearing threshold representative value from the assigned group when the ratio is less than the preset value of 1.3.

4. The auditory therapy frequency spectrum analysis apparatus of claim 1, wherein the assigned group is a first group from among the plurality of groups when all of the hearing threshold representative value for each of the n number of frequency bands are less than the lower limit.

5. The auditory therapy frequency spectrum analysis apparatus of claim 4, wherein the program instructions determine that no acoustic stimulus signal is to be generated when all of the hearing threshold representative values within the first group are lower than the predetermined limit.

6. The auditory therapy frequency spectrum analysis apparatus of claim 1, wherein the assigned group is a second group from among the plurality of groups when at least one of the hearing threshold representative value for each of the n number of frequency bands is greater than the lower limit and less than the upper limit.

7. The auditory therapy frequency spectrum analysis apparatus of claim 1, wherein the assigned group is a third group from among the plurality of groups when at least one of the hearing threshold representative value for each of the n number of frequency bands is greater than the upper limit.

8. The auditory therapy frequency spectrum analysis apparatus of claim 7, wherein each of the hearing threshold representative value for each of the n number of frequency bands in the third group is compared to a preset frequency band range.

9. The auditory therapy frequency spectrum analysis apparatus of claim 4, wherein when at least one of the hearing threshold representative value for each of the n number of frequency bands within the first group is higher than the predetermined limit, the auditory therapy frequency spectrum analysis apparatus is configured to sort the hearing threshold representative value for each of the n number of frequency bands within the first group in descending order such that a first hearing threshold representative value is above a second hearing threshold representative value, to compare a ratio between the first hearing threshold representative value and the second hearing threshold representative value to the preset value of 1.3, and to delete the second hearing threshold representative value from the assigned group when the ratio is less than the preset value of 1.3.

10. The auditory therapy frequency spectrum analysis apparatus of claim 8, wherein when a hearing threshold representative value in the third group belongs to the preset frequency band range, the auditory therapy frequency spectrum analysis apparatus is configured, to sort a first hearing threshold representative value within the third group in descending order above a second hearing threshold representative value within the third group, to compare a ratio between the first hearing threshold representative value and the second hearing threshold representative value to the preset value of 1.3, and to delete the second hearing threshold representative value from the assigned group when the ratio is less than the preset value of 1.3.

11. The auditory therapy frequency spectrum analysis apparatus of claim 8, wherein when a hearing threshold representative value in the third group does not belong to the preset frequency band range, the auditory therapy frequency spectrum analysis apparatus is configured to sort a first hearing threshold representative value within the third group in descending order above a second hearing threshold representative value within the third group, to compare a ratio between the first hearing threshold representative value and the second hearing threshold representative value to the preset value of 1.3, and to delete the second hearing threshold representative value from the assigned group when the ratio is less than the preset value of 1.3.

* * * * *